US006405079B1

United States Patent
Ansarinia (10) Patent No.: US 6,405,079 B1
(45) Date of Patent: Jun. 11, 2002

(54) STIMULATION METHOD FOR THE DURAL VENOUS SINUSES AND ADJACENT DURA FOR TREATMENT OF MEDICAL CONDITIONS

(76) Inventor: Mehdi M. Ansarinia, 349 Condon Ct., Santa Clara, CA (US) 95050

( * ) Notice: Subject to any disclaimer, the term of this patent is extended or adjusted under 35 U.S.C. 154(b) by 0 days.

(21) Appl. No.: 09/667,868

(22) Filed: Sep. 22, 2000

(51) Int. Cl.[7] .............................................. A61N 1/00
(52) U.S. Cl. ...................................................... 607/2
(58) Field of Search ........................... 607/2, 3, 44, 45, 607/46; 128/898

(56) References Cited

U.S. PATENT DOCUMENTS

| 4,856,526 A | 8/1989 | Liss et al. |
| 5,540,734 A | 7/1996 | Zabara |
| 5,938,688 A | 8/1999 | Schiff |

OTHER PUBLICATIONS

Frisardi et al., "Electric versus magnetic transcranial stimulation of the trigeminal system in healthy subjects. Clinical applications in gnathology." J Oral Rehabil vol. 24(12):920–928 (1997) (abstract).
Onofrio et al., "Surgical treatment of chronic cluster headache" Mayo Clin Proc vol. 61(7):537–544 (1986).
"Thalamic Stimulation" and "Trigeminal Neuralgia", Neuroscience Pathways (published by The Cleveland Clinic Foundation), Spring 1988 newsletter, pp. 1–2.
Taub et al., "Chronic electrical stimulation of the gasserian ganglion for the relief of pain in a series of 34 patients" J Neurosurg vol. 86:197–202 (1997).

Suzuki et al., "Selective electrical stimulation of postganglionic cerebrovascular parasympathetic nerve fibers originating from the sphenopalatine ganglion enhances cortical blood flow in the rat" J Cerebr Blood Flow and Metab vol. 10:383–391 (1990).
Young, "Electrical stimulation of the trigeminal nerve root for the treatment of chronic facial pain" J Neurosurg vol. 83:72–78 (1995).
Goadsby et al., "Differential effects of low dose CP122,288 and eletriptan on Fos expression due to stimulation of the superior sagittal sinus in cat" Pain 82:15–22 (1999).

(List continued on next page.)

Primary Examiner—Scott M. Getzow
(74) Attorney, Agent, or Firm—Finley & Berg LLP; Michael N. Berg (57) ABSTRACT

A method is provided for the suppression or prevention of pain, movement disorders, epilepsy, cerebrovascular diseases, autoimmune diseases, sleep disorders, autonomic disorders, urinary bladder disorders, abnormal metabolic states, disorders of the muscular system, and neuropsychiatric disorders in a patient. The method comprises positioning at least one electrode adjacent to or around an implantation site selected from the group consisting of the patient's: superior sagittal sinus; confluence of sinuses; occipital sinus; sigmoid sinus; transverse sinus; straight sinus; inferior sagittal sinus; the dura adjacent the superior sagittal sinus, confluence of sinuses, occipital sinus, sigmoid sinus, transverse sinus, straight sinus, or inferior sagittal sinus; or falx cerebri. The electrode is then activated to apply an electrical signal to the at least one implantation site. In a further embodiment of the invention used to treat the same conditions, the electrode dispenses a medication solution or analgesic to the implantation site. A method is also provided for surgically implanting the electrodes adjacent to or around the implantation site.

22 Claims, 3 Drawing Sheets

OTHER PUBLICATIONS

Browne et al., "Concurrent cervical and craniofacial pain" Oral Surg Oral Med Oral Path 86(6): 633–640 (Dec. 1998).

"Headache Classification Committee of the International Headache Society—Classification and diagnostic criteria for headache disorders, cranial neuralgias and facial pain" Cephalalgia Supp. & 0:13, 19–24, and 35–38 (1988).

Storer et al., "Microiontophoretic application of serotonin (5HT) 1B/1D agonists inhibits trigeminal cell firing in the cat" Brain 120:2171–2177 (1997).

Phebus et al., "The non–peptide NK–1 receptor antagonist LY303870 inhibits neurogenic dural inflammation in guinea pigs" Life Sciences 60(18):1553–1561 (1997).

Strassman et al., "Sensitization of meningeal sensory neurons and the origin of headaches" Nature 384:560–563 (Dec. 1996).

Hoskin et al., "Fos expression in the trigeminocervical complex of the cat after stimulation of superior sagittal sinus is reduced by L–NAME" Neuroscience Letters 266:173–176 (1999).

Goadsby et al., "The trigeminovascular system and migraine: studies characterizing cerebrovascular and neuropeptide changes seen in humans and cats" Ann Neurol 33:48–56 (1993).

Goadsby et al., "Stimulation of an intracranial trigeminally–innervated structure selectively increases cerebral blood flow" Brain Research 751:247–252 (1997).

Cutrer et al., "Effects of PNU–109,291, a selective 5H–T1D receptor agonist, on electrically induced dural plasma extravasation and capsaicin–evoked c–fos immunoreactivity within trigeminal nucleus caudalis" Neuropharm 38:1043–1053 (1999).

Carroll et al., "Motor cortex stimulation for chronic neuropathic pain: a preliminary study of 10 cases" Pain 84:431–437 (2000).

Schulz et al., "Localization of epileptic auras induced on stimulation by subdural electrodes" Epilepsia 38(12) 1321–1329 (1997).

Moskowitz et al., "Basic mechanisms in vascular headache" Headache 8(4):801–815 (Nov. 1990).

Goadsby et al., "Substance P blockade with the potent and centrally acting antagonist GR205171 does not effect central trigeminal activity with superior sagittal sinus stimuation" Neuroscience 86(1):337–343 (1998).

Feindel et al., "The tentorial nerves and localization of intracranial pain in man" Neurology 555–563 (1955).

Nguyen et al., "Chronic motor cortex stimulation in the treatment of central and neuropathic pain. Correlations between clinical, electrophysiological and anatomical data" Pain 82:245–251 (1999).

STIMULATION METHOD FOR THE DURAL VENOUS SINUSES AND ADJACENT DURA FOR TREATMENT OF MEDICAL CONDITIONS

FIELD OF THE INVENTION

The present invention relates generally to methods for suppressing or preventing medical conditions such as pain, movement disorders, sleep disorders, autonomic disorders, gastrointestinal disorders, and abnormal metabolic states.

BACKGROUND OF THE INVENTION

Headaches are one of the most common ailments, and afflict millions of individuals. The specific etiology of headaches may be difficult to pinpoint. Known etiology of headache pain include trauma and vascular, autoimmune, degenerative, infectious, drug and medication-induced, inflammatory (sarcoid), neoplastic (primary or metastatic), metabolic-endocrine, iatrogenic (such as post-surgical), muscloskelatal and myofascial causes. Even if the condition underlying the headache pain is identified and treated, headache pain may still persist.

Diagnosis of headache pain will typically include an identification of one or more categories of headaches. There are a variety of different headaches with different features. Migraine headaches, as defined by the International Headache Society (IHS) Classification, are typically unilateral, throbbing headaches lasting from four to seventy-two hours. Migraines are often accompanied by nausea, vomiting, light sensitivity and/or noise sensitivity. Females suffer from migraines more than males by an approximate ratio of 3:1. Migraine headaches can be further subdivided and subclassified into a number of different categories, such as, but not limited to, for example, migraine with aura, migraine without aura, transformed migraine, and retinal migraine.

Migraines have traditionally been treated with medications to prevent their recurrence and to alleviate acute pain and associated symptoms, such as nausea and vomiting. Non-invasive modalities of migraine treatment, which may be used alone or in combination, have included: diet modification, which may include the avoidance of known headache triggers (such as certain foods); biofeedback and relaxation techniques as well as other psychological modalities; acupuncture; chiropractic manipulation; and physical therapy. Invasive therapeutic procedures have also been implemented, and have included localized anesthetic blocks as well as neurosurgical interventions, such as nerve and ganglion transections and/or resections. However, use of those invasive techniques have typically been reserved for use in only in patients who have been unable to tolerate non-invasive procedures or who suffer from refractory headaches inadequately controlled with non-invasive methods, as they have been known to cause undesirable side effects and pose risks of infection and/or physiological damage to nerve tissues.

Currently, the highest known success rate (approximately seventy percent) in alleviating the pain of an acute migraine attack has been achieved using triptan class medications. Unfortunately, the effectiveness of each therapeutic modality typically varies widely between individual migraine sufferers, and irrespective of the treatment modality used, the suppression of migraine pain is often short-lived, with the pain recurring at levels which are typically less but sometimes equally or rarely more intense than before treatment. Many migraine sufferers find that their migraines are resistant to conventional treatment. In some cases, patients suffer from migraines on a continuous daily basis rather than on an episodic basis. Accordingly, a major emphasis for migraine treatment has been on prevention techniques.

Newer techniques for treating a variety of neurological disorders have included various electrical stimulation techniques. For example, U.S. Pat. No. 5,540,734 to Zabara describes a suggested therapeutic modality for a variety of medical, psychiatric and neurological disorders, including migraines, in which modulating electrical signals are applied to either or both of the trigeminal and glossopharyngeal nerves using electrodes. The principle behind these approaches is to disrupt or modulate abnormal neuronal transmissions in the nervous system through the application of the modulating electrical signals.

Cluster headaches are so termed due to their repeated occurrence in groups or clusters. Cluster headaches are much less common than migraines: migraine sufferers outnumber cluster headache sufferers by a ratio of approximately 100:1. Cluster headaches are characterized by intense, stabbing pain usually starting in the region of an eye or temple and localizing to one side of the face. Autonomic features such as lacrimation, nasal congestion, ptosis, conjunctival injection and pupillary changes are common in cluster headaches, which occur predominantly (approximately 90%) in males and usually start in the third or fourth decade of life. It is believed that the ingestion of alcohol may trigger the onset of cluster headaches.

IHS criteria indicate that episodic attacks of cluster headaches may last up to 90 minutes and may occur as many as six times per day. Cluster headaches typically occur in cycles lasting weeks to months and then spontaneously remit. Frequently, cluster headaches have a seasonal correlation, with their onset occurring more often in the fall and spring. While there are wide variations in the start of cluster headache cycles between headache sufferers, the cycles experienced by individual headache sufferers frequently follow a defined pattern with little deviation. The headaches usually occur at night, and often awaken the headache sufferer from sleep. It is not unusual for individual headache sufferers to experience the onset of cluster headaches at the same time during the night over repeated nights.

Because of the typically short duration of cluster headaches, therapies designed to abort the pain of an acute attack must have a quick onset of action. Such therapies have included oxygen inhalation, and injections of medication, such as dihydro ergotamine (DHE), ketorolac, or sumatriptan. Non-invasive therapies used to treat cluster headache pain and prevent their recurrence have included use of medications including ergot derivatives, varapamil, lithium, steroids, and sodium valproate; psychological intervention with biofeedback and relaxation techniques; and acupuncture. Anesthetic agents (such as Lidocaine) have been applied to the sphenopalatine ganglia, either directly, using a syringe, or indirectly, by soaking a long cotton swab in the anesthetic and placing the swab intranasally adjacent to the sphenopalatine ganglia, such that the anesthetic diffuses through the nasal mucosa to affect the SPG. Invasive approaches for the treatment of cluster headaches have included localized anesthetic block, surgical resection, radiofrequency, alcohol/phenol infiltration, radiosurgery and cryotherapy of the sphenopalatine ganglia and the trigeminal nerve and ganglion. The invasive approaches for treating cluster headaches are typically used only in headache sufferers who cannot tolerate the non-invasive methods of treatment, or in whom the cluster headaches are refractory and inadequately controlled with non-invasive methods.

Neuralgias, such as trigeminal, sphenopalatine, and occipital neuralgias, may start at any age, although trigeminal neuralgia is more common among the elderly. From a pathophysiological standpoint, pain arising due to neuralgias always originates from and is transmitted by the involved nerve. Accordingly, neuralgias may be caused by direct injury to nerves in the form of trauma, infection (such as herpes), neuroma formation or demyelination. Pain arising due to neuralgia may be brief and paroxysmal or continuous, and numerous attacks may occur throughout the day. Neuralgias do not feature seasonal or diurnal patterns in the onset of pain. In contrast to cluster headaches, trigeminal neuralgia often has an associated "trigger zone" on the face which can trigger the onset of the pain. Sphenopalatine neuralgia often has autonomic features, which are not commonly found in other neuralgias. In occipital neuralgia, the occipital nerve is usually tender to palpation and pain can be manifested anywhere along the course of the nerve.

Neuralgias, like migraines, have been treated using medication, invasive procedures, and, rarely, electrical stimulation of cranial nerves which are part of the central nervous system. None of the medications used in treating neuralgias have generally been effective in treating cluster headaches, other than sodium valproate.

The use of medications to treat the above-described conditions can result in systemic side-effects of wide-ranging severity. Invasive techniques used to destroy tissues, such as lesioning, resecting, freezing, or burning, are typically non-reversible, and the treatment cannot be adjusted once applied. Destruction of the nerve tissue may itself lead to significant side effects, such as deafferentation pain.

A primary object of the present invention is to provide an effective method for preventing, treating, or substantially suppressing headaches and related medical conditions.

A further object of the present invention is to provide a method for preventing or substantially suppressing pain and other medical conditions which can be utilized multiple times without successive invasive procedures.

Other objects and advantages of the current invention will become apparent when the inventive stimulation method is considered in conjunction with the accompanying drawings, specification and claims.

SUMMARY OF THE INVENTION

A method is provided for the suppression or prevention of pain, headache and its associated symptoms, movement disorders, epilepsy, cerebrovascular diseases, autoimmune diseases, sleep disorders, autonomic disorders, urinary bladder disorders, abnormal metabolic states, disorders of the muscular system, and neuropsychiatric disorders in a patient. The method comprises positioning at least one electrode adjacent to or around at least one implantation site selected from the group consisting of the patient's: superior sagittal sinus; confluence of sinuses; occipital sinus; sigmoid sinus; transverse sinus; straight sinus; inferior sagittal sinus; the dura adjacent to the superior sagittal sinus, confluence of sinuses, occipital sinus, sigmoid sinus, transverse sinus, straight sinus, or inferior sagittal sinus; or falx cerebri. The electrode is then activated to apply an electrical signal to the at least one implantation site.

In a further embodiment of the invention used to treat the same conditions, the electrode used is capable of being activated to dispense a medication solution or analgesic to the at least one implantation site.

A method is also provided for surgically implanting an electrode on or proximate to the at least one implantation site. The method comprises the steps of surgically opening an entry to the at least one implantation site, positioning and implanting an electrode adjacent to or around the at least one implantation site; and surgically closing the implantation site.

DESCRIPTION OF THE PREFERRED EMBODIMENT

Figure 1:
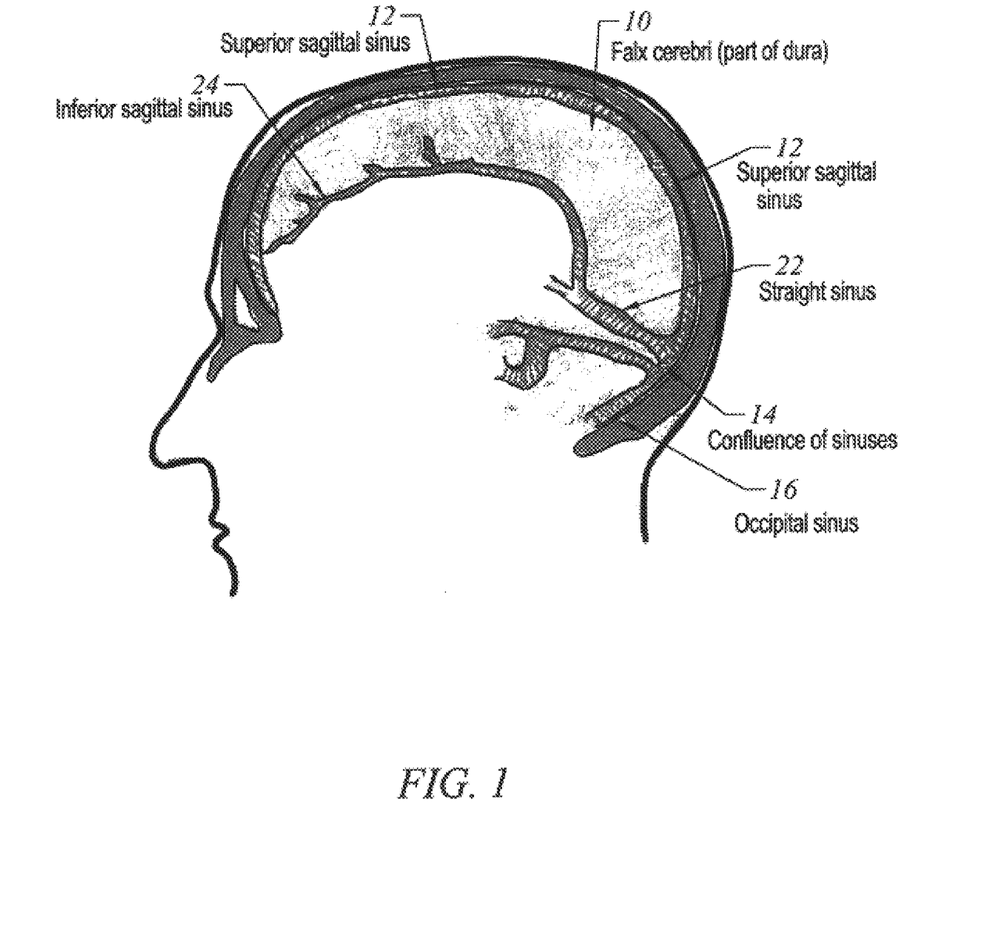
FIG. 1 is a schematic drawing of a cross-sectional lateral view of the skull showing a selection of the dural venous sinuses.
Figure 2:
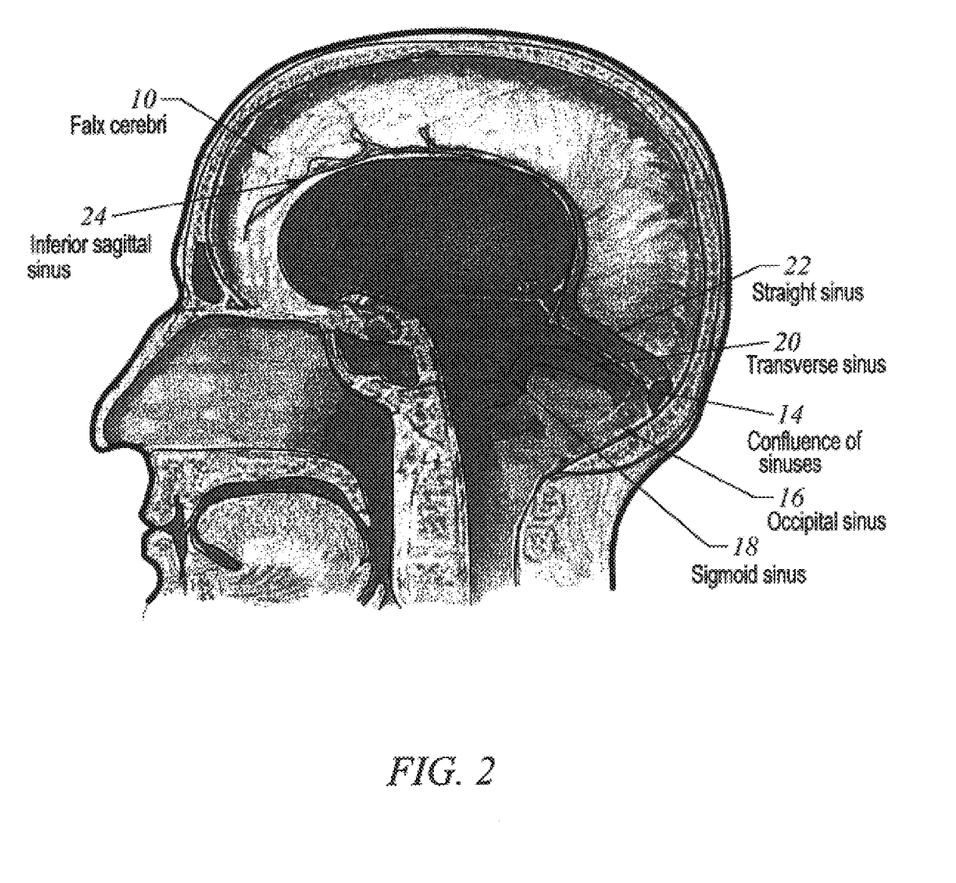
FIG. 2 is a schematic diagram of a cross-sectional lateral view of the skull showing dural venous sinuses and surrounding structures.

Referring to FIGS. 1 and 2, the inventive method utilizes direct and localized electrical stimulation of the venous sinuses and adjacent dura or falx cerebri 10 of the superior sagittal sinus 12 (FIG. 1), confluence of sinuses 14 (FIGS. 1 and 2), occipital sinus 16 (FIGS. 1 and 2), sigmoid sinus 18 (FIG. 2), transverse sinus 20 (FIG. 2); straight sinus 22 (FIGS. 1 and 2); inferior sagittal sinus 24 (FIGS. 1 and 2), or a combination thereof using one or more surgically implanted electrodes, for treatment of a number of medical conditions. Medical conditions which may be treated by the inventive method include, but are not limited to: pain (such as headache pain) and its associated symptoms, movement disorders, epilepsy, cerebrovascular diseases, autoimmune diseases, sleep disorders, autonomic disorders, urinary bladder disorders, abnormal metabolic states, disorders of the muscular system, and neuropsychiatric disorders.

Pain treatable by the inventive method may be caused by conditions including, but not limited to: migraine headaches, including migraine headaches with aura, migraine headaches without aura, menstrual migraines, migraine variants, atypical migraines, complicated migraines, hemiplegic migraines, transformed migraines, and chronic daily migraines; episodic tension headaches; chronic tension headaches; analgesic rebound headaches; episodic cluster headaches; chronic cluster headaches; cluster variants; chronic paroxysmal hemicrania; hemicrania continua; post-traumatic headache; post-traumatic neck pain; post-herpetic neuralgia involving the head or face; pain from spine fracture secondary to osteoporosis; arthritis pain in the spine, headache related to cerebrovascular disease and stroke; headache due to vascular disorder (such as atriovenous malformation); reflex sympathetic dystrophy, cervicalgia (which may be due to various causes, including, but not limited to, muscular, discogenic, or degenerative, including arthritic, posturally related, or metastatic); glossodynia, carotidynia; cricoidynia; otalgia due to middle ear lesion; gastric pain; sciatica; maxillary neuralgia; laryngeal pain, myalgia of neck muscles; trigeminal neuralgia (sometimes also termed tic douloureux); post-lumbar puncture headache; low cerebro-spinal fluid pressure headache; temporomandibular joint disorder; atypical facial pain; ciliary neuralgia; paratrigeminal neuralgia (sometimes also termed Raeder's syndrome); musculoskeletal neck pain; petrosal neuralgia; Eagle's syndrome; idiopathic intracranial hypertension; orofacial pain; myofascial pain syndrome involving the head, neck, and shoulder; chronic migraneous neuralgia, cervical headache; paratrigeminal paralysis; sphenopalatine ganglion neuralgia (sometimes also termed lower-half headache, lower facial neuralgia syndrome, Sluder's neuralgia, and Sluder's syndrome); carotidynia; Vidian neuralgia; and causalgia; or a combination of the above.

Movement disorders treatable by the inventive method may be caused by conditions including, but not limited to: Parkinson's disease; cerebral palsy; dystonia; essential tremor; and hemifacial spasms. Epilepsy treatable by the inventive method may be, for example, the various generalized or partial seizure disorders. Cerebrovascular disease treatable by the inventive method may be caused by conditions including, but not limited to: atherosclerosis, aneurysms, strokes, and cerebral hemorrhage. Autoimmune diseases treatable by the inventive method include, but are not limited to, multiple sclerosis. Sleep disorders treatable by the inventive method may be caused by conditions including, but not limited to: sleep apnea and parasomnias. Autonomic disorders treatable by the inventive method may be caused by conditions including, but not limited to: gastrointestinal disorders, including but not limited to gastrointestinal motility disorders, nausea, vomiting, diarrhea, chronic hiccups, gastroesphageal reflux disease, and hypersecretion of gastric acid; autonomic insufficiency; excessive epiphoresis; excessive rhinorrhea; and cardiovascular disorders including but not limited to cardiac dysrythmias and arrythmias, hypertension, and carotid sinus disease. Urinary bladder disorders treatable by the inventive method may be caused by conditions including, but not limited to: spastic or flaccid bladder. Abnormal metabolic states treatable by the inventive method may be caused by conditions including, but not limited to: hyperthyroidism or hypothyroidism. Disorders of the muscular system treatable by the inventive method include, but are not limited to, muscular dystrophy and spasms of the upper respiratory tract and face. Neuropsychiatric disorders treatable by the inventive method may be caused by conditions including, but not limited to: depression, schizophrenia, bipolar disorder, autism, personality disorders, and obsessive-compulsive disorder.

The pathophysiology creating the described medical conditions is not fully clear. For example, in the case of migraine headaches, a number of neurological and vascular events have been identified which take place prior to the onset of migraine pain. Research has indicated that a primary neuronal process triggers changes in dural vessels, which induces sterile inflammation that ultimately leads to activation of the trigeminal nucleus and the onset of head pain. Specifically, a wave of cortical depression suppresses cortical neuronal activity in the patient, followed by activation of migraine centers in the brain stem and perivascular inflammation commences. Dilation and constriction of cranial blood vessels may also occur. As the main pain sensitive structures in the brain are the large blood vessels, the venous sinuses, and the meninges, it is believed that the perivascular inflammation may be the main cause of head pain felt by migraine sufferers in many cases.

The large cerebral vessels, pial vessels, large venous sinuses and the surrounding dura are innervated by a plexus of nerve fibers (which are mostly unmyelinated) that arise from the trigeminal ganglion and the posterior fossa arising from the upper cervical dorsal nerve roots. This nerve fiber plexus is in the form of a sheath which wraps around the dural sinuses and blood vessels. Research has indicated that this nerve fiber plexus contains many inflammatory mediators, including substance P and calcitonin gene-related peptide. When the trigeminal ganglion is stimulated, the inflammatory mediators are released, causing sterile neurogenic inflammation of the perivascular space.

In previous research, tests on rats in which the trigeminal ganglion has been stimulated electrically or chemically have been shown to cause plasma extravasation and release of inflammatory mediators, increasing inflammation and associated pain symptoms. Further, such electrical and chemical stimulation has been shown to cause platelet aggregation, mast cell degranulation, sensitization of nerve terminals and endothelial activation, further commencing and propagating the neurogenic inflammatory cycle associated with migraines. The inventive method acts to disrupt neurogenic inflammation by stimulating the nerve fibers innervating the dural sinuses by using electrodes to deliver electrical stimuli and/or medication to one or more of the dural venous sinuses and/or the surrounding dura and falx cerebri in order to intercept signals passing through the nerve fibers which stimulate the neurogenic inflammation. This may occur by stimulating neurons which act to suppress the signals, by stimulating neurons which in turn activate other neurons acting to suppress the signals, by directly inhibiting the neurons which may stimulate the neurogenic inflammation, or a combination of the foregoing. Such stimulation may also act to disrupt the process by which inflammatory mediators such as vasoactive peptide are released from the afferent nerve fibers.

Additionally, the inventive method may also act to provide pain relief by disrupting pain signals transmitted through the nerve fibers even where neurogenic inflammation has commenced. Once neurogenic inflammation has commenced, the nerves become sensitized, and act as transducers changing chemical pain signals into electrical pain signals. The nerves then carry the generated electrical pain signals back to the trigeminal ganglion and then to the brainstem and brain pain centers, resulting in the perception of pain by the patient. The electrical stimuli and/or medication applied by electrodes to one or more of the dural venous sinuses and/or the surrounding dura and falx cerebri can influence and modulate the transduction of the chemical pain signals into electrical pain signals as well as suppress or prevent the transmission of the electrical pain signals.

In the preferred embodiment of the invention, one or more electrodes are surgically implanted directly adjacent to or around one or more implantation sites at the superior sagittal sinus 12 (FIG. 1), confluence of sinuses 14 (FIGS. 1 and 2), occipital sinus 16 (FIGS. 1 and 2), sigmoid sinus 18 (FIG. 2), transverse sinus 20 (FIG. 2); straight sinus 22 (FIGS. 1 and 2); inferior sagittal sinus 24 (FIGS. 1 and 2); or the adjacent dura or falx cerebri 10 (hereinafter termed "the implantation site"). For purposes of clarity, in the following discussion it shall be assumed that a single electrode is implanted within the patient. However, it should be understood that multiple electrodes may be implanted according to the inventive method, and that the characteristics discussed with respect to the single electrode apply equally to additional electrodes utilized. It should also be understood that the inventive method can be adapted to utilize devices other than electrodes, whether presently known or developed in the future, which can safely be utilized to provide the desired electrical stimulation or medication delivery to the implantation region.

The electrode is preferably controllable to produce output stimulating signals which can be varied in voltage, frequency, pulse width, current, and intensity. Further, the electrode is also preferably controllable such that the controller may produce both positive and negative current flow from the electrode, stop current flow from the electrode, or change the direction of current flow from the electrode. The electrode preferably also has the capacity for variable output, linear output, and short pulse width. While it is anticipated that a pulse generator will typically be used to control the electrode, it should be understood that any device or combination of devices may be used which allows the user to adjust the electrode as described above. The electrode should be anchored securely at the site of implantation within the patient so that the output signals produced by the electrode will consistently stimulate the same regions.

It is recommended that the application of stimulus from the electrode and adjustments of the electrode parameters as described above be done under the supervision and guidance of a physician. However, it should be understood that the inventive method may be applied such that the patient could, on the patient's initiative, activate the electrode to stimulate the desired region of stimulation. While it may be possible to configure the electrode and its controller such that the patient could alter the parameters of the electrode stimulus without supervision by a physician, this would not be recommended as the patient may not have sufficient knowledge to avoid dangers associated with misapplication of the inventive method.

The electrode will be connected to a power source (such as a battery or pulse generator) which provides the energy source for the electrical stimulation. The power source may be a battery implanted on or adjacent to the electrode, or the power source may be implanted at a remote site on the head or body away from the site of the electrical stimulation, as is currently done for power supplies for cardiac pacemakers and deep brain stimulators. The electrode is then connected to the remotely placed battery using wires. However, it should be understood that future technologies may be employed to provide alternative power sources. For example, it may become possible to obtain the energy needed to power the electrode directly from living tissues surrounding the electrode, such as nervous tissues, bony tissues, or fibrous tissues.

As the exact parameters of the signal stimulation which may be most effective for a particular patient may vary, in the preferred embodiment the electrode is controllable such that the electrode signal can be remotely adjusted to desired settings, so that no retrieval of the electrode from the patient is necessary to adjust the patient's therapy. Remote control of the electrode output can be effected, for example, using either conventional telemetry with an implanted electrical signal generator and battery or using an implanted radiofrequency receiver coupled to an external transmitter. It should be understood that as related technologies advance, other modalities for remote control of the electrode may be employed to adjust and modulate the electrode's parameters.

The electrode may be mono-polar, bipolar, or multi-polar. However, it is preferred that a multi-polar electrode be used as lower current levels are needed than for mono-polar or bipolar electrodes to produce equal stimulation levels. Unipolar stimulation typically utilizes a pole and a battery case as a ground, and requires relatively high amounts of current. Bipolar stimulation utilizes adjacent poles with current flowing from the negative pole (cathode) to the positive pole (anode), and causes depolarization of nervous tissue at lower current levels than for unipolar stimulation. The electrode and, if desired, any casing housing the electrode, are preferably made of inert materials (such as, for example, silicon, metal, or plastic), to reduce the risk of triggering an immune response by the patient to the implanted materials.

When stimulation is to be applied, the electrode is controlled to produce an electronic current wave. Preferably, the current wave will comprise relatively high frequency pulses with a low frequency amplitude modulation. While the exact parameters for the electrical stimulation of the implantation sites are not yet known and are likely to vary by patient, based upon data known for stimulations performed on the brain, spinal cord, and cranial nerves, optimal settings for stimulation of the implantation site may fall in the range of: a frequency of 0.1 to 2500 Hertz and preferably in the range of 5–200 Hertz, a pulse width of 20–1500 microseconds, an amplitude of 0.1 to 50 volts and preferably in the range of 0.1 to 20 volts, and an amplitude range of 0.1 to 50 milliamperes, preferably in the range of 0.5 to 15 milliamperes. The pulse separation for the stimulus may be set 500 microseconds, or may be made variable subject to the patient's response. Additionally, it may be effective to produce high frequency bursts of current on top of an underlying low frequency continuous stimulus. Preferably the electrode is associated with a programmable controller which may be utilized to produce continuous, scheduled, or episodic stimulation. Further, preferably the programmable controller can be utilized both to gradually increase stimulation to desired maximum levels or to immediately produce stimulation at the desired maximum level.

It should be understood that multiple methods may be used to surgically implant the electrode adjacent to or around the implantation site. Because the location of headache pain will vary from patient to patient, the precise location (or locations) at which the electrode (or electrodes) should be placed should be determined on an individual basis. Stimulation of the implantation site or sites is preferably performed at the time of the surgical implantation of the electrode or electrodes to identify the optimal stimulation site or sites for maximum pain relief.

The inventive method of surgical implantation preferably involves localization of at least one optimal implantation site, positioning the electrode adjacent to or around the optimal implantation site, and attaching the electrode to a power source. However, with regard to attaching the electrode to a power source, it should be understood that electrodes may be developed which make the implantation and/or attachment of a separate power source unnecessary. For example, an electrode may be used which contains its own power source, which is capable of obtaining sufficient power for operation from surrounding tissues in the patient's body, or which can be powered by bringing a power source external to the patient's body into contact with the patient's skin, such as at the cheek. In that case, the surgical procedure may be completed upon implantation of the electrode adjacent to or around the optimal stimulation site.

In the following discussion of methodologies which may be used to accomplish the surgical implantation of electrodes for the inventive method, it shall be assumed that the optimal stimulation site is the anterior one-third of the superior sagittal sinus 12 (see FIG. 1). However, referring to FIGS. 1 and 2, it should be understood that the described methodologies may be adjusted to place electrodes adjacent to or around the middle or posterior parts of the superior sagittal sinus 12, the confluence of sinuses 14, the occipital sinus 16, the sigmoid sinus 18, the transverse sinus 20, the straight sinus 22, the inferior sagittal sinus 24, the dura adjacent those sinuses or on the falx cerebri 10. For example, adjustments to the described methodologies needed to alter the implantation site may include, but are not limited to, changing: the positioning of the patient during implantation; the direction and size of incisions made; angles of approach of the instruments and equipment used; and the type of electrode used. For any selected stimulation site, the electrodes may be placed either ipsilateral or contralateral to the site of pain or discomfort, or may be placed bilaterally over or along the stimulation site.

Figure 3:
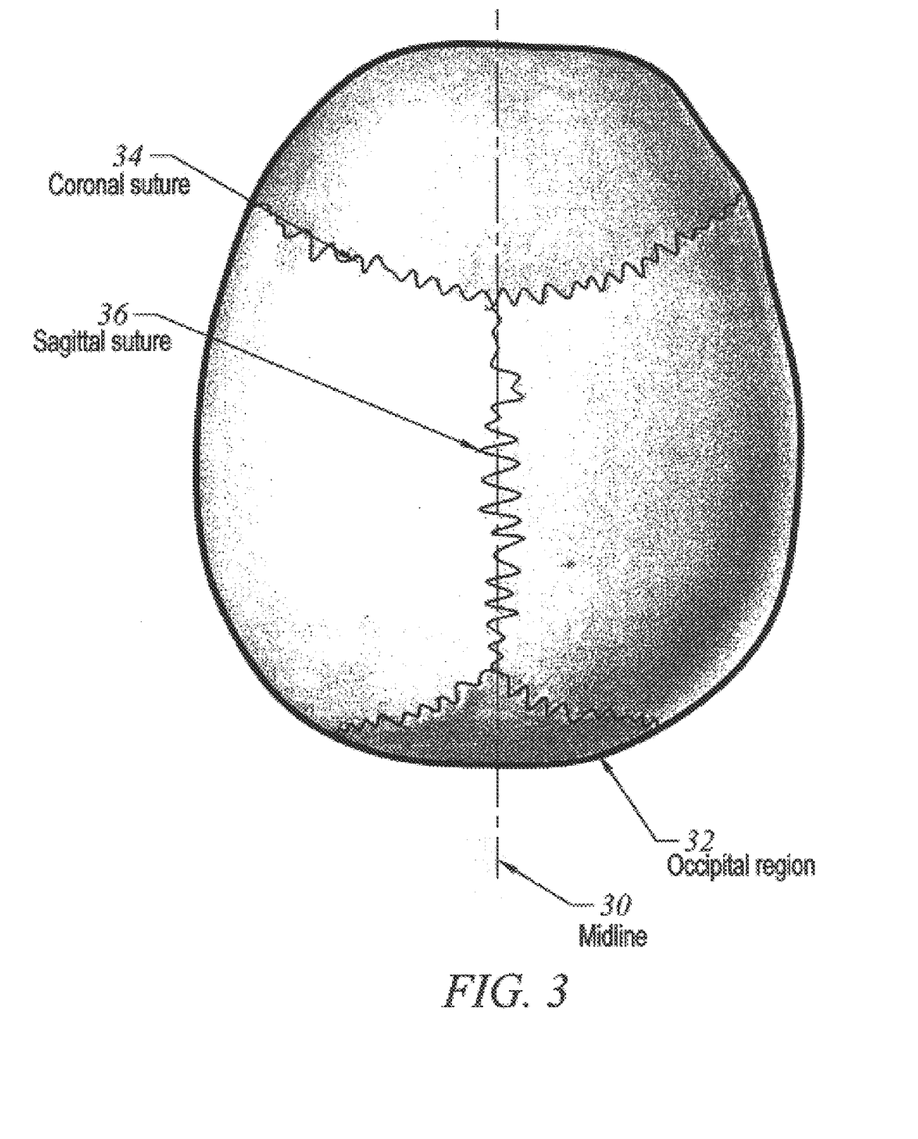
FIG. 3 is a top plan view of the skull showing various bone and suture structures of the skull.

At the commencement of the preferred procedure for implanting a stimulating electrode adjacent to or around the anterior one-third of the superior sagittal sinus 18, preferably the patient's head is shaved along the anterior portion of the superior sagittal sinus 18 three centimeters from the midline 30 (see FIG. 3) of the patient's skull. The occipital region 32 is also shaved on the side designated for surgery. Alternatively, the whole head may be shaven. The patient is then placed in the supine position on the operating room table and the patient's head is placed on a donut head holder with the head slightly flexed. Adhesive tape is preferably used to stabilize the head. The patient's head is then prepped for surgery, locally sterilized, and then draped in conventional fashion. A subcutaneous local anesthetic (such as, for example, a 1:1 mixture of lidocaine and 0.25% marcaine) is injected into the scalp, and additionally, the patient is preferably given intravenous sedation (such as propofol) and prophylactic antibiotics.

Once the anesthetic, intravenous sedation, and/or antibiotics have taken effect, a curvilinear or horseshoe shaped incision is made behind the patient's hair line. Bipolar cautery and raney clips are used conventionally to achieve hemostasis of the scalp and the periosteum covering the bone is dissected to expose the bone. A self retaining retractor is placed into the incision opening. The coronal suture 34 as well as the sagittal sutures 36 are identified.

Next, the desired implantation site, here the anterior one-third of the superior sagittal sinus 12, should be localized and made accessible. A first method which can be used to identify and access the desired implantation site may be termed the craniotomy method. In this method, two burr holes are first made on the coronal suture 34 at points two centimeters lateral to the midline 30 on each side. An additional burr hole is made at the midline 30 at a point approximately five centimeters anterior to the plane of the coronal suture 34. Bone wax is preferably used to achieve bone hemostasis in a conventional manner. To enable removal of the portion of the cranium to be removed in the craniotomy, the dura attaching to the cranium below the burr holes is dissected to separate the dura from the cranium using a dissecting instrument such as a Penfield Number 3. A high speed drill with a foot plate may then be used to make a rectangular craniotomy connecting the burr holes, with the superior burr holes forming the top corners of the rectangle and the inferior burr hole in the midline of the patient's head corresponding to the midpoint of the inferior side of the rectangle. The rectangular portion of the cranium is then removed to expose the anterior one-third of the superior sagittal sinus 12 (see FIG. 1). At this point, gelfoam and bipolar cautery may be used conventionally to achieve epidural hemostasis. Using a small drill bit, four holes are made in the bone adjacent to the craniotomy site and the dura should be attached to the four holes, for example by using sutures such as 4-0 neurolon sutures, to position the dura so that it does not intrude into the implantation site or sites.

A second method which can be used to identify and access the desired implantation site may be termed the burr hole method. In this method, referring to FIG. 3, the sagittal 36 and the coronal 34 sutures are first identified by palpation. Then two burr holes are made on the midline of the patient's head: one at the juncture point between the midline and the coronal suture, and the other five centimeters anterior to the first burr hole along the midline. Bone wax may be used conventionally to achieve hemostasis. As described in relation to the craniotomy method, the dura attaching to the cranium below the burr holes is dissected to separate the dura from the cranium using a dissecting instrument such as a Penfield Number 3. The anterior one-third of the superior sagittal sinus 12 (see FIG. 1) can then be visualized and accessed under the burr holes.

Use of the craniotomy method may be preferable where it is desired to implant a large number of electrodes or where previous scans of the patient's cranial anatomy (such as by MRI) indicate anatomical abnormalities, as the removal of a portion of the cranium allows for easier access to the implantation site for both implantation and diagnosis. The burr hole method may be preferable where a smaller number of electrodes are to be implanted and pre-surgery testing indicates few or no abnormalities which might interfere with implantation and that the particular locale of the desired implantation site is known, as the burr hole method requires less manipulation of the cranium and dura.

In both the craniotomy and burr hole methods of identifying and accessing the implantation site, intraoperative fluoroscopy and image-guided navigation using CT and/or MRI may be used to assist in the identification of the superior sagittal sinus 12 and other adjacent structures.

Once the craniotomy or burr hole method has been completed to identify and create access to the anterior one-third of the superior sagittal sinus 12, the electrode or electrodes desired for implantation are positioned at the implantation site. In a preferred embodiment, two plate electrodes are placed on the dorsal aspect of the superior sagittal sinus 12 along its longitudinal aspect. Alternatively, with a revision of the location of the burr holes, the plate electrodes can be placed such that they cover and traverse the entire dorsal aspect of the superior sagittal sinus 12, with the electrodes positioned in the transverse plane perpendicular to the axis of the superior sagittal sinus 12. Suitable plate electrodes may be obtained from the Medtronics Corporation as the Medtronic quadripolar electrode, Resume II, model 3587. However, it should be understood that alternative electrodes (for example, Medronics Corporation's Octet electrode number 3998 or other mono-, bi-, or multi-polar electrodes) may be used. Further, one or more electrodes may be used, either singly, or in an array of grid electrodes, depending on the number of desired stimulation sites. Additionally, it should be understood that where multiple electrodes are used, the electrodes may be placed at differing angles in relation to one another again depending on the selected desired stimulation sites. Alternative desirable electrode placements include: placing electrodes along the sides of the superior sagittal sinus 12 on either side of the midline 30 (see FIG. 3), which may be ipsilateral or contralateral to the side of headache pain, bilateral, across the dorsal aspect of the superior sagittal sinus (e.g. in parallel to the coronal plane), or along the longitudinal axis of the superior sagittal sinus. It should be understood that should it be desired that electrode placement be made only on one side of the superior sagittal sinus 12, the size of the craniotomy (in the craniotomy method) or the number of burr holes (in the burr hole method) may be reduced accordingly so that only the site on the desired side is exposed.

If the burr hole method is used, the electrode or electrodes may be positioned at the desired implantation site by passing them from the posterior burr hole towards the anterior burr hole until the tip of each electrode becomes visible at the anterior burr hole. As in the burr hole method, no portion of the cranium is removed during the procedure, the dura does not require dissection away from the cranium beyond the extent of the burr hole. Accordingly, the dura will typically hold the electrodes in place without the need for further anchoring of the electrodes.

In the craniotomy method, as the portion of the cranium and the dura overlying the implantation site are removed, the electrodes may simply be placed at the desired implantation site. However, as the dura has been dissected using this method, it will typically be necessary to anchor the electrodes to maintain them in the desired location. This may be accomplished by suturing the electrodes to the superficial layer of the dura, for example with a 4-0 neurolon or similar suture material.

Once the electrode or electrodes are positioned correctly and anchored, if necessary, the distal portion of the electrode, which consists of a wire, is then preferably connected to a hand held pulse generator/stimulator device for testing. A suitable pulse generator/stimulator device may be obtained from the Medtronics Corporation as dual screener 3628. The pulse generator/stimulator is then used to stimulate the electrodes so that the functioning of the electrodes may be tested at the implantation site and side effects may be assessed. At this stage of the operation, any sedation given to the patient previously (e.g. propofol) should have minimal effect such that the patient is sufficiently alert to report the effectiveness of the treatment and the existence of side effects. It is anticipated that suitable stimulation characteristics used for this testing include the following ranges: a frequency of 0.1 to 2500 Hertz and preferably in the range of 5–200 Hertz, a pulse width of 20–1500 microseconds, an amplitude of 0.1 to 50 volts and preferably in the range of 0.1 to 20 volts, and an amplitude range of 0.1 to 50 milliamperes, preferably in the range of 0.5 to 15 milliamperes. The pulse separation for the stimulus may be set 500 microseconds, or may be made variable subject to the patient's response.

If testing indicates that the electrode placement is not optimal, the electrode may be repositioned and testing recommenced. Once testing indicates that a desirable electrode placement has been achieved, steps are commenced to rewire the electrode to an attachment point in the occipital region. A percutaneous temporary connecting wire is inserted underneath the scalp adjacent to the site of the electrode. The distal end of the temporary connecting wire is then tunneled laterally towards the occipital region A one centimeter incision is made in the scalp in the occipital region. Blunt dissection of the soft tissue around the incision is made to form an occipital subcutaneous pocket. Gelfoam and bipolar cautery may be used conventionally to achieve hemostasis.

The distal end of the temporary connecting wire is then guided toward the incision site at the occipital subcutaneous pocket and pushed out of the incision site. The distal portion of the electrode is then disconnected from the hand held pulse generator/stimulator and attached to the proximal portion of the temporary connecting wire. A plastic sleeve is placed around the connection between the distal portion of the electrode and the proximal portion of the temporary connecting wire, completing the wiring for temporary stimulation.

If the craniotomy approach was used, the removed portion of the cranium can then be reattached to the skull. Preferably, this is done by placing the removed portion of the cranium over the dura and attaching the removed portion of the cranium to the adjacent bone conventionally using, for example, four two hole plates with 4 mm screws. The four holes made with the small drill bit may be used in attaching the plate to the adjacent bone. The galea is then closed, for example, using inverted interrupted 3-0 Vicryl sutures. The skin over the craniotomy site is then closed, for example, using staples. The occipital incision is then sutured close around the distal portion of the percutaneous temporary connecting wire and sterile dressing is applied.

The portable pulse generator/stimulator is then connected to the distal end of the percutanous temporary connecting wire, which at this time should be protruding out of the patient's skull at the occipital region. Further test trials of the electrode can now be performed by stimulating the electrodes using multiple contacts, which may be either positive or negative.

For testing purposes it is desirable to trigger the onset of the condition which the stimulation is designed to alleviate. For example, headache pain and associated conditions such as nausea may be induced using a variety of triggers, including but not limited to: a 0.4 mg nitroglycerin sublingual tablet; ingestion of chocolate; or consumption of caffeinated beverages. Testing of stimulation of the electrode may then be recommenced, preferably using the parameter ranges discussed previously in relation to the immediate testing of the electrodes after implantation. Depending on the patient's needs, the testing period may last for several days until the effective stimulation parameters for the individual patient are discovered.

Once the trial period is completed, the patient is taken back to the operating room. If the trial is not successful, the incisions may be reopened and the electrodes removed, with the cranium portion, galea and skin closed as discussed above to complete the surgery.

In patients with successful test-trials, the wiring of the electrodes is then made permanent for further treatment. The patient is put under general anaesthesia and placed in supine position on the operating table. A shoulder roll is placed to stabilize the patient's body and the patient's head is placed on a doughnut roll with the head turned to the left or the right depending on the side of the head in which the pulse generator is to be implanted. All pressure points are padded accordingly in conventional fashion and prophylactic antibiotics are given as required. The occipital region, neck, and the chest are shaved, prepared in sterile fashion (for example. using betadien) and draped in the conventional sterile fashion.

The distal end of the percutaneous temporary connecting wire is pulled out from the patient's skull and cut flush to the skin, thereby bringing the proximal end of the percutaneous temporary connecting wire along with the distal end of the electrode into the occipital subcutaneous pocket. Additional sterile prepping and draping is performed as required, and the incision site at the occipital subcutaneous pocket is opened. The connection between the distal portion of the electrode and the proximal portion of the percutanous temporary connecting wire is located and the plastic sleeve around this connection is removed. A hex wrench is used to separate the distal portion of the electrode from the proximal portion of the percutanous temporary connecting wire, and the proximal portion of the percutaneous temporary connecting wire is removed from the surgical field.

Next, a five centimeter longitudinal incision is made in the patient's chest at the infraclavicular region or along the anterior axillary line. The subcutaneous tissue below the longitudinal incision is dissected until the pectoralis fascia is identified. A subcutaneous pocket is then made in the pectoralis fascia for a permanent pulse generator/stimulator. A suitable permanent pulse generator/stimulator may be obtained from the Medtronics Corporation as the Itrel III. A percutaneous tunneler, such as the tunneler 3550-06 available from the Medtronics Corporation, is then used to connect the occipital subcutaneous pocket to the chest subcutaneous pocket. A permanently implantable connector wire, such as wire model 7495 available from the Medtronics Corporation, is tunneled from the chest to the occipital region. The proximal portion of the permanently implantable connector wire is then attached to the distal end of the electrode and secured with a hex wrench. A plastic sleeve is placed over the connection between the implantable connector wire and the distal end of the electrode, and ties, such as 2 2-0 Tevdkek ties available from the Medtronics Corporation are tied at both ends of the plastic sleeve. The distal aspect of the permanently implantable connector wire is then placed securely into the pulse generator/stimulator and tightened with the hex wrench. The pulse generator/stimulator is sutured to the pectoralis fascia, for example using 2 2-0 silk sutures, and the occipital incision is closed using sutures.

It should be understood that the pulse generator/stimulator may be implanted at other areas of the body if so desired.

To complete the surgical procedure, all wounds are irrigated with copious amounts of antibiotic solution. The deep layer is closed with inverted interrupted sutures, and the skin closed with staples. Dry, sterile dressings are placed on all wounds.

Electrodes may be implanted which instead of or in addition to delivering electric stimulation, deliver a medication solution or analgesic to the implantation site. In that case, in order to infuse solutions of medications into the electrode, a medication pump and reservoir are preferably implanted next to the pulse generator/stimulator. The medication pump should have a battery, and the medication reservoir should have a port extending subcutaneously which can be easily identified by palpation of the client's skin. This port may then be used to refill the reservoir with more medication solution as needed. The parameters for the infusion including rate of infusion, time of infusion and the other parameters can be preset but may be changed with the aid of external programming devices. Although the foregoing invention has been described in some detail by way of illustration for purposes of clarity of understanding, it will be readily apparent to those of ordinary skill in the art in light of the teachings of this invention that certain changes and modifications may be made thereto without departing from the spirit or scope of the appended claims.

It is claimed:

1. A method for suppressing or preventing pain, movement disorders, epilepsy, cerebrovascular diseases, autoimmune diseases, sleep disorders, autonomic disorders, urinary bladder disorders, abnormal metabolic states, disorders of the muscular system, and neuropsychiatric disorders in a patient, the method comprising:
   positioning at least one electrode adjacent to or around at least one implantation site, said at least one implantation site selected from the group consisting of the patient's: superior sagittal sinus; confluence of sinuses; occipital sinus; sigmoid sinus; transverse sinus; straight sinus; inferior sagittal sinus; the dura adjacent the superior sagittal sinus, confluence of sinuses, occipital sinus, sigmoid sinus, transverse sinus, straight sinus, or inferior sagittal sinus; or falx cerebri;
   activating the at least one electrode to apply an electrical signal to the at least one implantation site.

2. The method of claim 1 wherein the at least one electrode is surgically implanted adjacent to or around the at least one implantation site.

3. The method of claim 2 wherein the electrical signal applied by the electrode can be adjusted in voltage, frequency, pulse width, current, or intensity.

4. The method of claim 3 wherein the electrical signal applied by the electrode may be made positive or negative and the direction of current flow from the electrode may be changed.

5. The method of claim 4 wherein the at least one electrode may be remotely controlled using a remote control device which is accessible from outside the body of the patient.

6. The method of claim 5 wherein the at least one electrode is powered by a power source surgically implanted within the patient.

7. The method of claim 6 wherein the at least one electrode is multi-polar.

8. The method of claim 6 wherein the at least one electrode is unipolar.

9. The method of claim 6 wherein the at least one electrode is bipolar.

10. The method of claim 7 wherein the electrical signal applied by the at least one electrode has a frequency in the range of from about 0.1 to 2500 Hertz, a pulse width in the range of from about 20 to 1500 microseconds, an amplitude in the range of from about 0.1 to 50 volts, and an amplitude in the range of from about 0.1 to 50 milliamperes.

11. The method of claim 1 wherein activation of the at least one electrode is done to treat:
   (i) pain resulting from one or more medical conditions comprising: migraine headaches, including migraine headaches with aura, migraine headaches without aura, menstrual migraines, migraine variants, atypical migraines, complicated migraines, hemiplegic migraines, transformed migraines, and chronic daily migraines; episodic tension headaches; chronic tension headaches; analgesic rebound headaches; episodic cluster headaches; chronic cluster headaches; cluster variants; chronic paroxysmal hemicrania; hemicrania continua; post-traumatic headache; post-traumatic neck pain; post-herpetic neuralgia involving the head or face; pain from spine fracture secondary to osteoporosis; arthritis pain in the spine, headache related to cerebrovascular disease and stroke; headache due to vascular disorder; musculoskeletal neck pain; reflex sympathetic dystrophy, cervicalgia; glossodynia, carotidynia; cricoidynia; otalgia due to middle ear lesion; gastric pain; sciatica; maxillary neuralgia; laryngeal pain, myalgia of neck muscles; trigeminal neuralgia; post-lumbar puncture headache; low cerebro-spinal fluid pressure headache; temporomandibular joint disorder; atypical facial pain; ciliary neuralgia; paratrigeminal neuralgia; petrosal neuralgia; Eagle's syndrome; idiopathic intracranial hypertension; orofacial pain; myofascial pain syndrome involving the head, neck, and shoulder; chronic migraneous neuralgia, cervical headache; paratrigeminal paralysis; sphenopalatine ganglion neuralgia; carotidynia; Vidian neuralgia; and causalgia;
   (ii) movement disorders resulting from one or more medical conditions comprising: Parkinson's disease; cerebral palsy; dystonia; essential tremor; and hemifacial spasms;
   (iii) epilepsy, including generalized and partial seizure disorder;
   (iv) cerebrovascular diseases resulting from one or more medical conditions comprising: atherosclerosis, aneurysms, strokes, and cerebral hemorrhage;
   (v) autoimmune diseases resulting from one or more medical conditions comprising multiple sclerosis;
   (vi) sleep disorders resulting from one or more medical conditions comprising sleep apnea and parasomnias;
   (vii) autonomic disorders resulting from one or more medical conditions comprising: gastrointestinal disorders, including but not limited to gastrointestinal motility disorders, nausea, vomiting, diarrhea, chronic hiccups, gastroesphageal reflux disease, and hypersecretion of gastric acid; autonomic insufficiency; excessive epiphoresis; excessive rhinorrhea; and cardiovascular disorders including but not limited to cardiac dysrythmias and arrythmias, hypertension, and carotid sinus disease;
   (viii) urinary bladder disorders resulting from one or more medical conditions comprising spastic or flaccid bladder;
   (ix) abnormal metabolic states resulting from one or more medical conditions comprising hyperthyroidism or hypothyroidism
   (x) disorders of the muscular system resulting from one or more medical conditions comprising muscular dystrophy and spasms of the upper respiratory tract and face; and (xi) neuropsychiatric disorders resulting from one or more medical conditions comprising: depression, schizophrenia, bipolar disorder, autism, personality disorders, and obsessive-compulsive disorder.

12. A method for suppressing or preventing pain, movement disorders, epilepsy, cerebrovascular diseases, autoimmune diseases, sleep disorders, autonomic disorders, urinary bladder disorders, abnormal metabolic states, disorders of the muscular system, and neuropsychiatric disorders in a patient, the method comprising:

positioning at least one electrode adjacent to or around at least one implantation site, said at least one implantation site selected from the group consisting of the patient's: superior sagittal sinus; confluence of sinuses; occipital sinus; sigmoid sinus; transverse sinus; straight sinus; inferior sagittal sinus; the dura adjacent the superior sagittal sinus, confluence of sinuses, occipital sinus, sigmoid sinus, transverse sinus, straight sinus, or inferior sagittal sinus; or falx cerebri;

said electrode capable of dispensing a medication solution or an analgesic;

activating the at least one electrode to apply the medication solution or analgesic to said at least one implantation site.

13. The method of claim 12 wherein the at least one electrode is surgically implanted adjacent to or around said at least one implantation site.

14. The method of claim 13 wherein the amount of medication solution or analgesic applied, the rate at which medication solution or analgesic is applied, and the time period over which the medication solution or analgesic is applied can be adjusted.

15. The method of claim 14 wherein the at least one electrode may be remotely controlled using a remote control device which is accessible from outside the body of the patient.

16. The method of claim 15 wherein the at least one electrode is powered by a power source surgically implanted within the patient.

17. The method of claim 12 wherein activation of the at least one electrode is done to treat:

(i) pain resulting from one or more medical conditions comprising: migraine headaches, including migraine headaches with aura, migraine headaches without aura, menstrual migraines, migraine variants, atypical migraines, complicated migraines, hemiplegic migraines, transformed migraines, and chronic daily migraines; episodic tension headaches; chronic tension headaches; analgesic rebound headaches; episodic cluster headaches; chronic cluster headaches; cluster variants; chronic paroxysmal hemicrania; hemicrania continua; post-traumatic headache; post-traumatic neck pain; post-herpetic neuralgia involving the head or face; pain from spine fracture secondary to osteoporosis; arthritis pain in the spine, headache related to cerebrovascular disease and stroke; headache due to vascular disorder; reflex sympathetic dystrophy, cervicalgia; glossodynia, carotidynia; cricoidynia; otalgia due to middle ear lesion; gastric pain; sciatica; maxillary neuralgia; laryngeal pain, myalgia of neck muscles; trigeminal neuralgia; post-lumbar puncture headache; low cerebro-spinal fluid pressure headache; temporomandibular joint disorder; atypical facial pain; ciliary neuralgia; paratrigeminal neuralgia; petrosal neuralgia; Eagle's syndrome; idiopathic, intracranial hypertension; orofacial pain; myofascial pain syndrome involving the head, neck, and shoulder; chronic migraneous neuralgia, cervical headache; paratrigeminal paralysis; sphenopalatine ganglion neuralgia; carotidynia; Vidian neuralgia; and causalgia;

(ii) movement disorders resulting from one or more medical conditions comprising: Parkinson's disease; cerebral palsy; dystonia; essential tremor; and hemifacial spasms;

(iii) epilepsy, including generalized and partial seizure disorder;

(iv) cerebrovascular diseases resulting from one or more medical conditions comprising: atherosclerosis, aneurysms, strokes, and cerebral hemorrhage;

(v) autoimmune diseases resulting from one or more medical conditions comprising multiple sclerosis;

(vi) sleep disorders resulting from one or more medical conditions comprising sleep apnea and parasomnias;

(vii) autonomic disorders resulting from one or more medical conditions comprising: gastrointestinal disorders, including but not limited to gastrointestinal motility disorders, nausea, vomiting, diarrhea, chronic hiccups, gastroesphageal reflux disease, and hypersecretion of gastric acid; autonomic insufficiency; excessive epiphoresis; excessive rhinorrhea; and cardiovascular disorders including but not limited to cardiac dysrythmias and arrythmias, hypertension, and carotid sinus disease;

(viii) urinary bladder disorders resulting from one or more medical conditions comprising spastic or flaccid bladder;

(ix) abnormal metabolic states resulting from one or more medical conditions comprising hyperthyroidism or hypothyroidism (x) disorders of the muscular system resulting from one or more medical conditions comprising muscular dystrophy and spasms of the upper respiratory tract and face; and (xi) neuropsychiatric disorders resulting from one or more medical conditions comprising: depression, schizophrenia, bipolar disorder, autism, personality disorders, and obsessive-compulsive disorder.

18. A method for surgically implanting an electrode adjacent to or around at least one implantation site, said at least one implantation site selected from the group consisting of the patient's: superior sagittal sinus; confluence of sinuses; occipital sinus; sigmoid sinus; transverse sinus; straight sinus; inferior sagittal sinus; the dura adjacent the superior sagittal sinus, confluence of sinuses, occipital sinus, sigmoid sinus, transverse sinus, straight sinus, or inferior sagittal sinus; or falx cerebri; the method comprising:

surgically opening an entry to the at least one implantation site;

positioning and implanting an electrode adjacent to or around the at least one implantation site; and surgically closing the implantation site.

19. The method of claim 18 further comprising the step of attaching said electrode to an external power source.

20. The method of claim 18 wherein said electrode contains its own power source.

21. The method of claim 18 wherein said step of surgically opening an entry to the at least one implantation site comprises performing a craniotomy removing a portion of the cranium above the implantation site.

22. The method of claim 18 wherein said step of surgically opening an entry to the at least one implantation site comprises making one or more burr holes in the patient's skull such that an electrode may be passed through said one or more burr holes and positioned at the implantation site.

* * * * *